(12) United States Patent
Jean-Pierre

(10) Patent No.: US 7,295,890 B2
(45) Date of Patent: Nov. 13, 2007

(54) PRESCRIPTION DRUG COMPLIANCE MONITORING SYSTEM

(75) Inventor: Richard Jean-Pierre, Plymouth, MN (US)

(73) Assignee: StrataMed Labs, Inc., Plymouth, MN (US)

( * ) Notice: Subject to any disclaimer, the term of this patent is extended or adjusted under 35 U.S.C. 154(b) by 431 days.

(21) Appl. No.: 10/670,595

(22) Filed: Sep. 25, 2003

(65) Prior Publication Data
US 2004/0133305 A1 Jul. 8, 2004

Related U.S. Application Data

(60) Provisional application No. 60/411,013, filed on Sep. 26, 2002.

(51) Int. Cl.
*G06F 17/00* (2006.01)
(52) U.S. Cl. .................. 700/244; 700/231; 700/232
(58) Field of Classification Search ......... 700/231–244
See application file for complete search history.

(56) References Cited

U.S. PATENT DOCUMENTS

| 4,504,153 | A | * | 3/1985 | Schollmeyer et al. ......... 368/10 |
| 4,725,997 | A |   | 2/1988 | Urquhart et al. |
| 4,748,600 | A |   | 5/1988 | Urquhart |
| 4,768,176 | A | * | 8/1988 | Kehr et al. ................... 368/10 |
| 5,016,172 | A |   | 5/1991 | Dessertine |
| 5,016,230 | A |   | 5/1991 | Seifers et al. |
| 5,020,037 | A |   | 5/1991 | Raven |
| 5,233,571 | A |   | 8/1993 | Wirtschafter |
| 5,289,157 | A |   | 2/1994 | Rudick et al. |
| 5,313,439 | A |   | 5/1994 | Albeck |
| 5,392,952 | A | * | 2/1995 | Bowden ....................... 221/15 |
| 5,408,443 | A |   | 4/1995 | Weinberger |
| 5,602,802 | A |   | 2/1997 | Leigh-Spencer et al. |
| 5,646,912 | A |   | 7/1997 | Cousin |
| 5,706,257 | A |   | 1/1998 | Rothman et al. |
| 5,751,661 | A |   | 5/1998 | Walters |
| 5,852,590 | A |   | 12/1998 | de la Huerga |
| 5,917,429 | A |   | 6/1999 | Otis, Jr. et al. |
| 6,032,155 | A | * | 2/2000 | de la Huerga ........... 707/104.1 |
| 6,084,504 | A |   | 7/2000 | Rosche et al. |
| 6,239,712 | B1 | * | 5/2001 | Hawk ....................... 340/686.1 |
| 6,259,654 | B1 | * | 7/2001 | de la Huerga ................. 368/10 |
| 6,271,753 | B1 | * | 8/2001 | Shukla ..................... 340/545.6 |
| 6,302,295 | B1 | * | 10/2001 | Weisman ..................... 221/188 |

(Continued)

FOREIGN PATENT DOCUMENTS

EP  0 298 627 A2  1/1989

(Continued)

OTHER PUBLICATIONS www.aardex.ch, MEMS Medication Management System.

*Primary Examiner*—Gene O. Crawford
*Assistant Examiner*—Michael K Collins
(74) *Attorney, Agent, or Firm*—Shumaker & Sieffert, P.A.

(57) ABSTRACT

The drug compliance monitoring system provides a patient with a portable medication dispenser programmed with medication-taking data. The dispenser alerts the patient to take a dose of medication and gathers compliance data relating to the medication-taking data. The compliance data is accessible to a physician, or other care givers, etc., via a network database.

20 Claims, 13 Drawing Sheets

U.S. PATENT DOCUMENTS

| | | | |
|---|---|---|---|
| 6,317,390 B1 * | 11/2001 | Cardoza | 368/10 |
| 6,324,123 B1 * | 11/2001 | Durso | 368/10 |
| 6,332,100 B1 * | 12/2001 | Sahai et al. | 700/242 |
| 6,335,907 B1 * | 1/2002 | Momich et al. | 368/10 |
| 6,424,599 B1 | 7/2002 | Ditzig | |
| 6,529,446 B1 * | 3/2003 | de la Huerga | 368/10 |
| 6,564,121 B1 * | 5/2003 | Wallace et al. | 700/231 |
| 6,594,549 B2 | 7/2003 | Siegel | |
| 6,604,650 B2 * | 8/2003 | Sagar | 221/3 |
| 6,633,796 B1 * | 10/2003 | Pool et al. | 700/231 |
| 6,702,146 B2 * | 3/2004 | Varis | 221/3 |
| 6,707,763 B2 | 3/2004 | Osberg et al. | |
| 6,771,165 B2 * | 8/2004 | Burg II et al. | 340/384.1 |
| 6,953,039 B2 * | 10/2005 | Scarrott et al. | 128/200.14 |
| 2001/0009398 A1 | 7/2001 | Sekura et al. | |
| 2002/0027507 A1 | 3/2002 | Yarin et al. | |
| 2002/0169635 A1 | 11/2002 | Shillingburg | |
| 2007/0073560 A1 * | 3/2007 | Walker et al. | 705/3 |

FOREIGN PATENT DOCUMENTS

| | | |
|---|---|---|
| EP | 0 265 049 B1 | 1/1993 |
| WO | WO 95/09386 | 4/1995 |
| WO | WO 00/32097 | 6/2000 |

\* cited by examiner

ISP INFORMATION

PHONE:  (612) 555-1212
LOGIN : SYNERGISTECH
PASS:   LABS

| RIGHT ARROW | + | − | OK |

FIG. 7

| GEORGE W. BUSH | |
|---|---|
| AMOXICILLIN | 2/13/0 |
| 23  MAY  08 : 03a | OK |
| 08 : 00p | MISSED |
| 24  MAY  08 : 13a | OK |
| 08 : 00p | OK |

| BACK | UP ARROW | DOWN ARROW | DETAILS |

FIG. 11

PRESCRIPTION DRUG COMPLIANCE MONITORING SYSTEM

This application claims the benefit under 35 U.S.C. § 119(e) of U.S. Provisional Application No. 60/411,013 filed on Sep. 26, 2002, for PRESCRIPTION DRUG COMPLIANCE MONITORING SYSTEM, which is incorporated by reference.

BACKGROUND OF THE INVENTION

The present invention relates generally to healthcare monitoring systems and methods and, more particularly, to a system and method for dispensing and monitoring medication for healthcare treatment.

A 1995 American Association of Retired Persons study reported that Americans age 65 and older are taking an average of 2.4 prescription drugs, while those age 50-64 take an average of 1.7 prescription drugs. It is also reported that 40% of those failed to follow their physician's dosage instructions. The Healthcare Compliance Package Council states that of the 1.8 billion prescriptions per year dispensed in the U.S., 50% are not correctly taken. The article that discussed this topic was featured in the September 1998 edition of the Packaging Digest Magazine. From the same source it is also reported that more than 80% of the current 36.3 million people over age 65 in the United States, a number that is sure to increase, are on some type of prescription medication-taking regimen. According to the National Medical Expenditure Survey, in 1987, 90 million Americans suffered from one or more chronic conditions. Treatment of these chronic conditions represents over 76% of healthcare expenditures, and the total direct cost of treating these chronic conditions is estimated to rise to $798 billion in 2030.

These statistics clearly depict the usefulness of a system to help patients comply with their medication-taking regimen while limiting their risk of potential adverse complications. As a result of compliance, the patient is in a better position to control their treatment recovery time. Remembering to accurately take medication on time and correctly is well understood to be a very serious health problem, particularly for the elderly and patients with chronic conditions for whom the intake of many different drugs is common. Failure to comply with medication-taking regimens is associated with deterioration of health status, as well as an increase in preventable fatalities. The annual cost related to non-compliance with medication-taking regimens was estimated to be in excess of $100 billion in 1998.

The drop off rate for refilling medications for chronic diseases is very high, with up to 75% of monthly prescriptions not refilled after one year. Forgetfulness to self-administer the prescribed medication at the correct intervals and correct dosages by the patients has long been found to be a major hurdle for doctors in determining the effectiveness of prescriptions. It is also well known that the more frequently a medication must be taken, the more likely the patient's compliance rate will drop. For patients who must take three, four or even five dosages of several medications daily, the prescribed regimen can easily become confusing. Many patients resort to carrying daily timetables—pill containers that sort out the medication by day of the week, or they even rely on somebody else to tell them when to take their medication. This can be effective but does not eliminate the possibility of the patient becoming distracted or simply forgetful in addition to the lack of a reliable compliance record.

Various devices for assisting patients in following medication-taking regimens are known. For example, U.S. Pat. No. 6,294,999 to Yarin et al. describes a smart tray with a plurality of medication containers equipped with electromagnetic tags that provides various information about medication contained within a respective container. The smart tray is equipped with a processor and reader that interrogates each respective electromagnetic tag to identify medication contained within each container. Using the retrieved information, a smart tray provides visual and/or audio signals to a patient to remind the patient when and how much of various medicaments to take. The device can also communicate with one or more third parties, such as healthcare providers, pharmacies, and other suppliers of healthcare products and services via a computer network. In addition, a smart tray can communicate with various appliances and can modify medication regimens for particular situations in response to data received from various appliances.

U.S. Pat. No. 5,020,037 to Raven discloses an alarm pillbox which cancels the alarm when a compartment lid is opened. A visual display is used to indicate the number of times that the lid has been opened within one day.

U.S. Pat. No. 5,408,443 to Weinberger describes a medication-dispensing system that includes a prescribing data entry station for use by a physician to store prescription information in a portable prescribing module, a dispensing data entry station for use by a pharmacy to store dispensing information in a portable dispensing data storage unit, and a medication dispenser responsive to information stored in the portable prescribing module to describe use of medication in the dispenser in accordance with a regimen prescribed by the physician and to the dispensing data storage unit to control dispensing of the medication. One embodiment has two medication drawers each having a plurality of compartments with indicating lights selectively indicating the compartment from which medication is to be taken, a screen for displaying instructions regarding loading of the medication compartments and taking of the medication, and a keyboard for confirming compliance with the instructions. Another embodiment has a series of medication-containing compartments, each covered by a separate sliding or folding cover.

U.S. Pat. No. 4,911,327 to Shepherd et al., describes a dispenser for providing scheduled dosages of pills according to a predetermined medication program. A housing contains a plurality of pill containers from which dosages of pills may be released into a user-accessible pill receiver. The release of pills is controlled such that pills are released at predetermined intervals as dictated by the medication program. On release of a dosage of pills, an alarm is activated to indicate to a user that a dosage is due to be taken, the alarm being deactivated when the user accesses the pill receiver to remove the dosage of pills. If the user does not access the pill receiver within a predetermined time interval from release of the dosage, an optional remote alarm may be activated to alert a supervisor.

U.S. Pat. No. 5,239,491 to Mucciacciaro describes a holder having a plurality of recesses for holding a plurality of medication containers, each fitting into a unique recess. The geometry of the bottom of each medication container is unique and only matches one recess in the holder. A sensor in each recess signals the presence or absence of the dedicated container to a microprocessor. The microprocessor is programmed with the prescribed dose administration schedule for each of the different medications in the different containers. A real time clock cooperates with the microprocessor and the program to signal audibly and visibly by a light in the appropriate container when a particular pill should be administered. The signals stop when the appropriate container is removed from its recess. A different warning sound indicates when the wrong container is lifted.

U.S. Pat. No. 4,837,719 to McIntosh describes a medication clock for signaling the times that dosages of a medication should be taken. The McIntosh device also provides a record of when each medication was taken for comparison with the medication schedule. In addition, the McIntosh device can monitor and record temperature, blood pressure and pulse rate of the user.

U.S. Pat. No. 4,616,316 to Hanpeter et al. describes a medication compliance monitoring system consisting of a blister pack having an array of plastic blisters defining compartments for medication. The blister pack has a frangible non-conductive backing sheet including conductive traces behind the compartments, which are respectively ruptured when the medication doses are removed. An electronic memory circuit detects when individual compartments are ruptured and stores this information.

E-pill (www.epill.com) offers a pager system that sends reminders to patients to take their medication at a specific time of the day. Carebridge (www.carebridge.net) provides an electronic timing device that patients can use to help them remember to take their medication.

IBV Technologies (Seattle, Wash.) provides a medication vial that records the time a patient takes his/her medication when a button is pressed by the patient. When returned to a pharmacy for a refill, the pharmacist can download and review a compliance report from the vial and counsel the patient regarding medication compliance.

APREX (Union City, Calif.) provides a telemedline service for monitoring medication compliance. Patients take their medication from medication containers outfitted with caps that have a microcomputer therein. When patients remove the cap from a bottle to take a dose of the medication contained therein, the microcomputer records the time and date of the dosing event. At the end of the day, patients place their medication bottles on a specially configured modem that transmits daily dosing information to a selected healthcare provider. If the healthcare provider detects a problem in how or when patients are taking their medication, specially trained healthcare providers call those patients the next day.

The MediMonitor, available from InforMedix, Inc. (Rockville Md.), is configured to retain a month supply of up to five medications in individual compartments and alerts patients when and how to take the medications. The MediMonitor also monitors medication use and health status by providing a date and time-stamped record of a patient's medication-taking behavior together with patient responses to specific questions. MediMonitor can transmit information via an internet-accessible server and database to clinical drug trial sites, physicians, pharmacies and other healthcare providers. Healthcare providers can communicate information, as well as reminders and specific instructions, directly to patients via the MediMonitor.

Unfortunately, existing devices for assisting patients in following medication-taking regimens can be somewhat non-accessible to the public due to price and difficult to use because of their complexity. Furthermore, existing devices for assisting patients in following medication-taking regimens can seem somewhat intrusive to a user.

BRIEF SUMMARY OF THE INVENTION

The present invention is directed to a system and method for aiding with compliance of a medication-taking regimen and improving self-reliance and independence of patients. A base station and portable cap assembly attached to a medication container assist the user in remembering to take medication at different period intervals during the course of complying with a medication-taking regimen. The system is also capable of storing in memory the specific time and date of an event for later retrieval by a care giver.

The present invention may facilitate compliance with medication regimens, especially complex regimens involving multiple medications. As such, the present invention may reduce medication errors made by patients such as forgetting to take a dosage, confusing dosage times, taking more medication or various combinations thereof.

BRIEF DESCRIPTION OF THE DRAWINGS

FIG. 7 is a Set ISP Information screen.
FIG. 11 is a Medication History screen.

DETAILED DESCRIPTION

Figure 1:
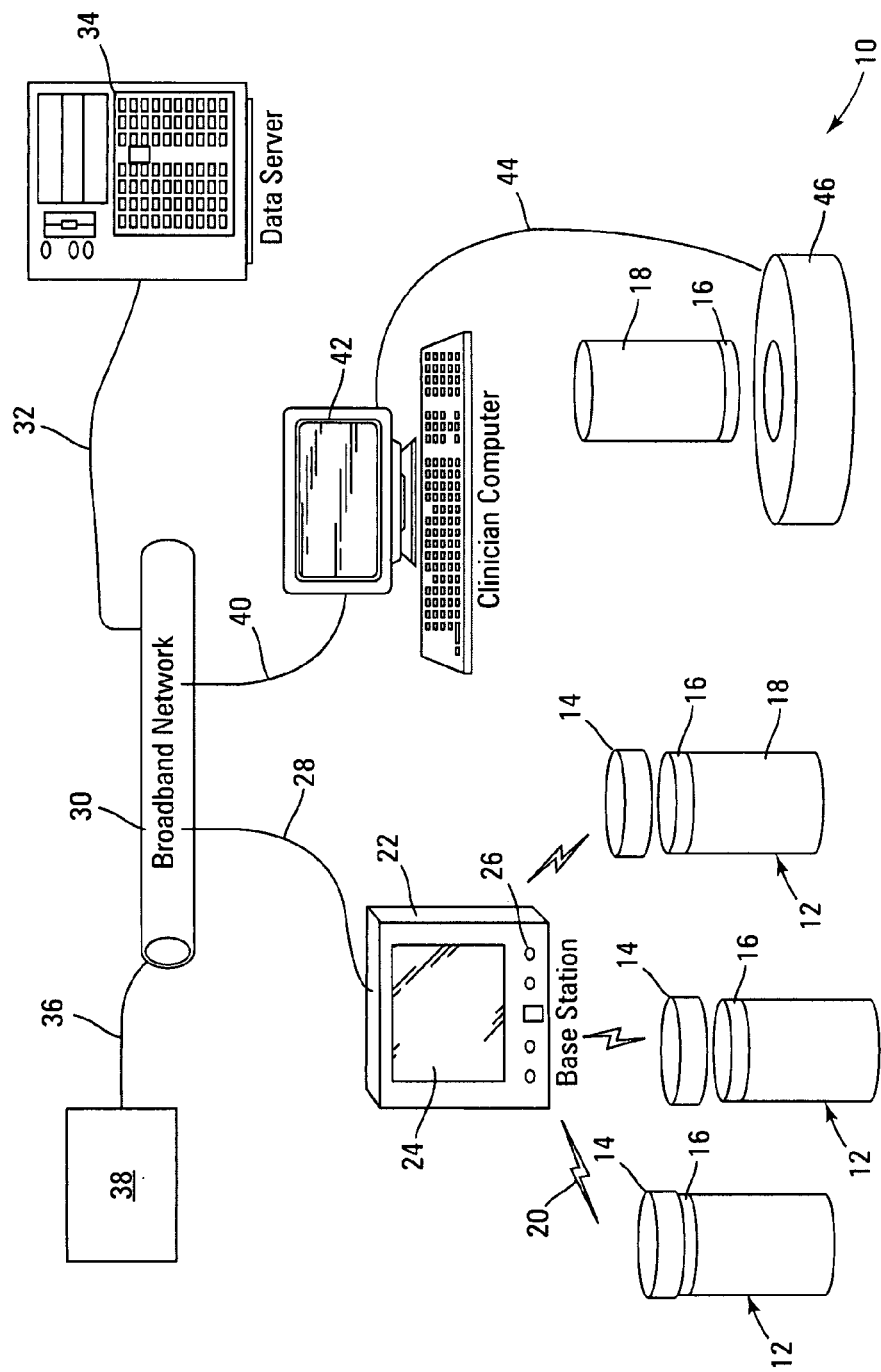
FIG. 1 is a diagram of the medication compliance system.

FIG. 1 shows medical compliance system 10 of the present invention. System 10 includes portable medication dispenser 12 having cap 14, collar 16, and container 18; communication link 20; base station 22 having LCD 24 and user interface keys 26; communication link 28; network 30; line 32; data server 34; communication link 36; remote terminal 38; communication link 40; remote terminal 42; line 44; and programming base 46.

Dispenser 12 is comprised of cap 14 which is removably attached to collar 16. Collar 16 is removably connected to the opening of container 18. Three dispensers 12 are shown in FIG. 1. One is shown with cap 14 attached to collar 16. Two are shown with cap 14 detached from collar 16.

Cap 14 communicates with base station 22 by communication link 20. Base station 22 has LCD 24 and a bank of user interface keys 26. Base station 22 communicates with data network 30 via line 28. Data network 30 is also linked to data server 34 by line 32, remote terminal 38 by line 36, and remote terminal 42 by line 40. Remote terminal 42 communicates with programming station 46 through line 44. FIG. 1 also includes an inverted container 18 attached to collar 16, which couples to programming station 46.

For simplicity, the present invention will be described in the context of a physician prescribing a medication to a patient. However, the invention may be used by any party wishing to induce and/or track a person's compliance with a medication-taking regimen.

In operation, collar 16 contains memory and is connected to container 18 and then coupled with programming station 46 such that medication-taking data is downloaded to collar 16. Medication-taking data includes a medication-taking regimen and prescription information, the patient's name, the physician's name, or any other data that may be required. The physician calls the prescription in to a pharmacist that is equipped with remote terminal 42 linked to programming station 46, or the details of the prescription may be entered manually by the care giver or pharmacist. The pharmacist inserts collar 16 into programming station 46 and enters the medication-taking data into remote terminal 42, which subsequently downloads the data through line 44 and programming station 46 to collar 16. The connection represented by line 44 is preferably an interface cable making contact between remote terminal 42 and programming station 46. Container 18 is subsequently filled with medication, cap 14 is attached to collar 16, and dispenser 12 is given to the patient.

Cap 14 contains a microcontroller, an indicator, a sensor, and communication means. The microcontroller accesses the medication-taking regimen stored in the memory of collar 16, when the two are attached, to activate the indicator when the patient should take a dose of medication. It also gathers compliance data from the sensor, which senses if the patient is complying with the medication-taking regimen. The compliance data is also stored in the memory of collar 16.

The patient is equipped with base station 22. When linked by link 20, cap 14 transmits the medication-taking data along with the compliance data to base station 22. Preferably, link 20 is a form of wireless communication, such as infrared light emitting diode, radio frequency, near magnetic field, etc. Base station 22 then transmits the compliance data through line 28 to network 30, which uses data server 34 to store all of the data. Line 28 may be any type of link for communication with a network, such as the Internet, Intranet, a Wide Area Network (WAN), or a Local Area Network (LAN).

The physician can subsequently access the compliance data from a remote location. The physician uses remote terminal 38 to access the data from network 30 through link 36, which again is any type of communication link. Thus, an outside party, such as a physician, can determine if the patient is complying with the medication-taking regimen. In an alternative embodiment, remote terminal 42 may be used to both input the medication-taking data to collar 16 and access the compliance data. In either instance, access to compliance data is greatly simplified for both the physician and patient.

Figure 2:
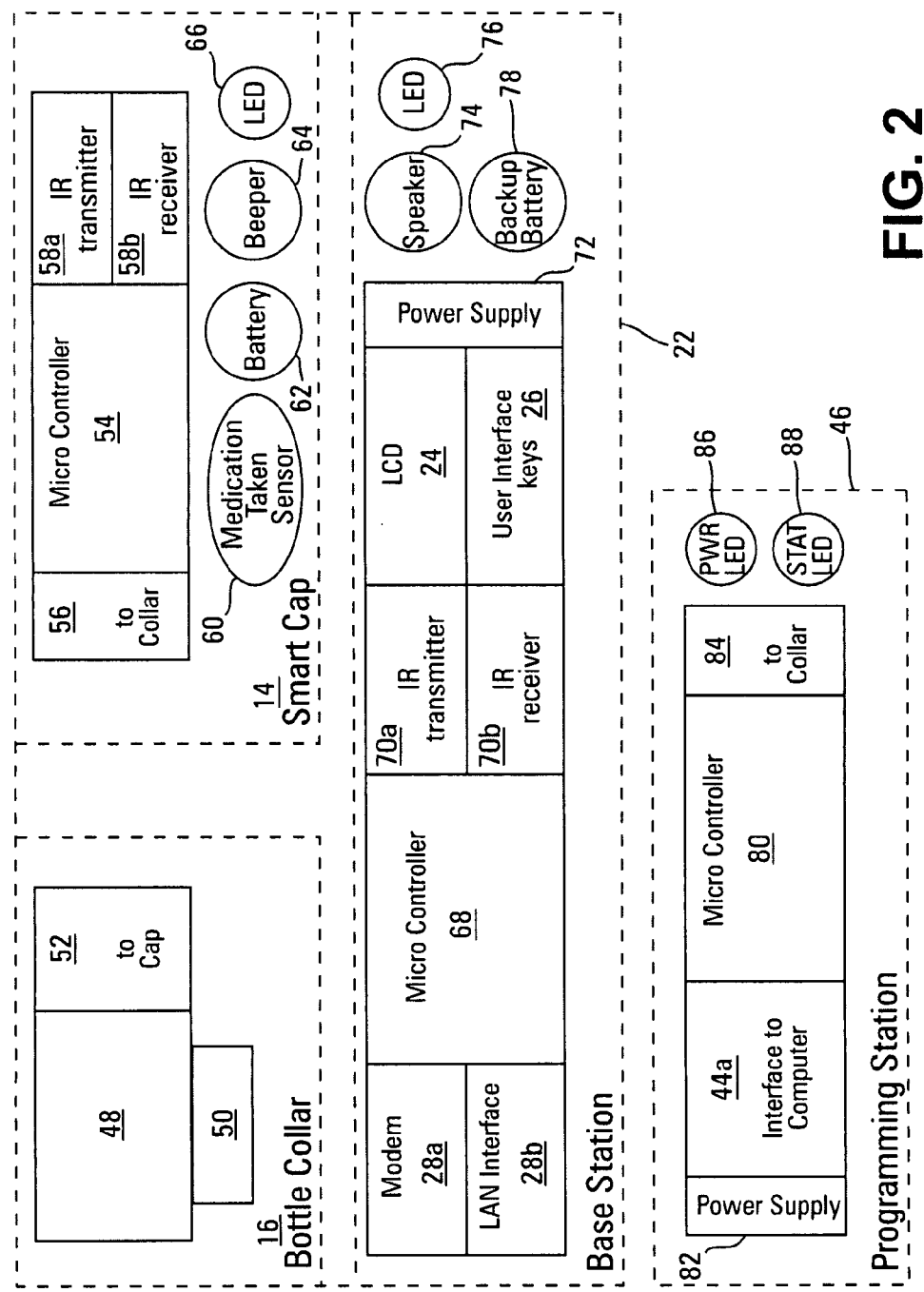
FIG. 2 is a block diagram of the preferred embodiment of the medication compliance device.

FIG. 2 shows a block diagram of cap 14, collar 16, base station 22, and programming station 46. Cap 14 and collar 16 form a portable cap assembly. Collar 16 includes memory 48 and connectors 50 and 52. Cap 14 includes microcontroller 54, connector 56, IR transmitter 58a, IR receiver 58b, sensor 60, battery 62, audio indicator 64, and visual indicator 66. Base station 22 includes LCD 24, user interface keys 26, modem 28a, interface 28b, microcontroller 68, IR transmitter 70a, IR receiver 70b, power supply 72, speaker 74, LED 76, and back up battery 78. Programming station 46 includes interface 44a, microcontroller 80, power supply 82, connector 84, power LED 86, and status LED 88.

The patient keeps base station 22 at their residence. Power supply 72 powers base station 22 through an AC outlet, and backup battery 78 when power is cut off. Base station 22 has either or both modem 28a and interface 28b for connection to network 30. Various screens are displayed on LCD 24 for programming and displaying data and instructions for complying with the medication-taking regimen. These are discussed in further detail below.

A pharmacist receives a prescription for a medication-taking regimen from a physician. Collar 16 is detached from cap 14 and placed adjacent the opening of container 18. Collar 16 comes in a variety of sizes to accommodate various sized openings of containers 18, and both collar 26 and container 18 are disposable and are only used once. Container 18 with collar 16 is then coupled to programming station 46 (FIG. 1), which is linked to remote terminal 42 via interface 44a. Collar 16 and programming station 46 communicate via connectors 50 and 84, respectively. Connector 50 is preferably a 4-pin connector. Power LED 86 indicates whether there is adequate power to supply programming station 46, and status LED 88 indicates whether collar 16 is properly inserted into programming station 46.

The pharmacist inputs the medication-taking data to memory 48 of collar 16. Container 18 is filled with a medication, and cap 14 is attached to collar 16. Cap 14 is reusable and can be used for more than one use. Dispenser 12, consisting of container 18, collar 16, and cap 14, is given to the patient. In an alternative embodiment, the pharmacist may be able to download the medication-taking data to base station 22, which would subsequently transmit the information to dispenser 12.

The patient places dispenser 12 in the vicinity of base station 22 so that cap 14 communicates with base station 22 through wireless communication link 14 (FIG. 1). Preferably, wireless communication is via an infrared light emitting diode. To this end, cap 14 is equipped with IR transmitter 58a and IR receiver 58b, and base station 22 is equipped with IR transmitter 70a and IR receiver 70b. Any type of communication link may be used, but wireless communication is preferred. All of the medication-taking data is transmitted to base station 22.

Collar 16 and cap 14 communicate through connectors 48 and 56, respectively. Battery 62 powers cap 14. Microcontroller 54 reads and carries out the medication-taking regimen stored in memory 48. When it is time for the patient to take a medication, either or both of audio indicator 64 and visual indicator 66 are activated. Indicators may be of any type that will alert the patient that a dose of medication should be taken and include audio, visual, and tactile indicators. Indicators 64 and 66 are activated for 15 minutes or until sensor 60 receives a signal indicating compliance. Preferably, audio indicator 64 is a buzzer that emits a 200 ms buzz every 30 seconds, and visual indicator 66 is an LED that blinks at a rate of 1 Hz, 25% duty cycle. Either of indicators 64 and 66 may also indicate low battery life.

When cap 14 is within range of communicating with base station 22 and it is time to take a dose of medication, cap 14 instructs visual indicator 76 to activate similarly to visual indicator 66. Accordingly, audio indicator 74 is instructed to activate similarly to audio indicator 64. Base station 22 may also be equipped with a speaker, not shown, that provides a synthesized voice to remind the patient to take their medication.

If the patient takes the medication within the allotted time for compliance, sensor 60 senses that a dose of medication was taken. Microcontroller 54 notes that a dose of medication was taken and stores the date and time in memory 48. In most cases, sensor 60 detects inferentially that a dose of medication was taken by noting some form of handling of container 18. For example, sensor 60 may detect the opening/closing of dispenser 12 or that dispenser 12 was inverted. Any means for sensing and generating a detectable electrical signal may be used.

If sensor 60 does not sense that a dose was taken, microcontroller 54 notes that the patient did not comply with the medication-taking regimen. The time of non-compliance is noted and stored in memory 48. If the missed medication dose is taken at a later time, that time is noted and stored in memory 48. Data from sensor 60 is the compliance data, which is subsequently transmitted to base station 22.

Figure 3:
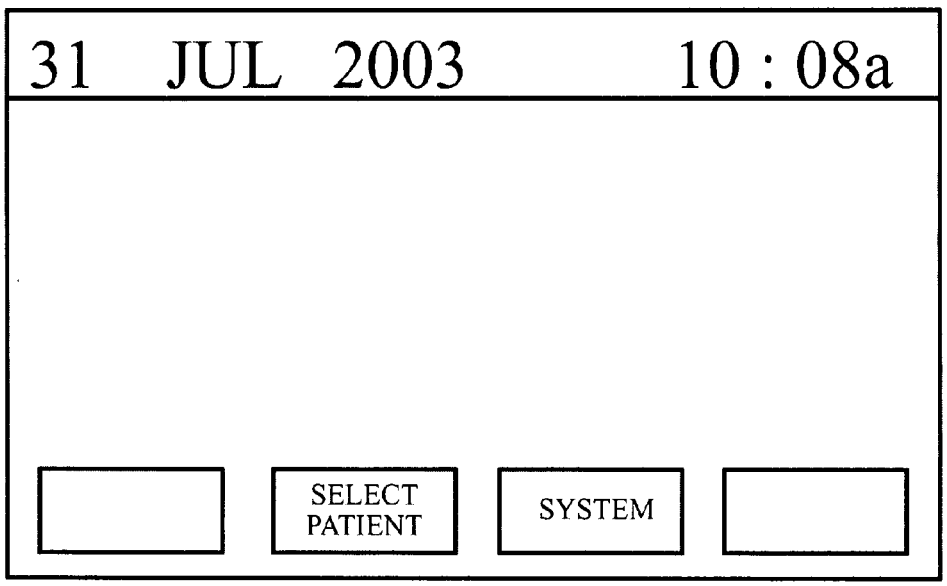
FIG. 3 is a Main Menu screen.

Base station 22 has user interface keys 26, preferably four keys adjacent to LCD 24, for navigating the various screens. Keys 26 operate as soft keys, such that the function of each key changes based on the screen that is displayed. After a power-up and a splash screen are displayed, a Main Menu screen is displayed as shown in FIG. 3. The Main Menu screen always updates the current date and time. The Main Menu screen also shows messages to the patient when necessary (i.e. George Bush take 2 tablets of Claritin).

Figure 4:
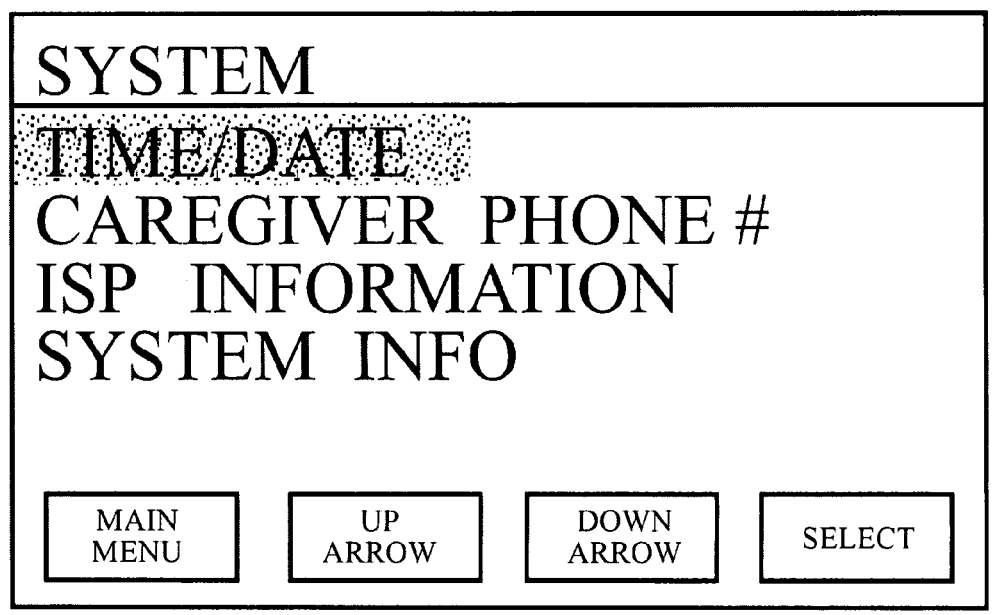
FIG. 4 is a System screen.

When the patient presses the System key on the Main Menu screen, the System screen shown in FIG. 4 is displayed. The System screen lists various system settings that the patient can edit. One system setting in the list is highlighted at a time, and Up Arrow and Down Arrow keys move the highlight up and down the list, respectively. The Main Menu key returns to the Main Menu screen.

Figure 5:
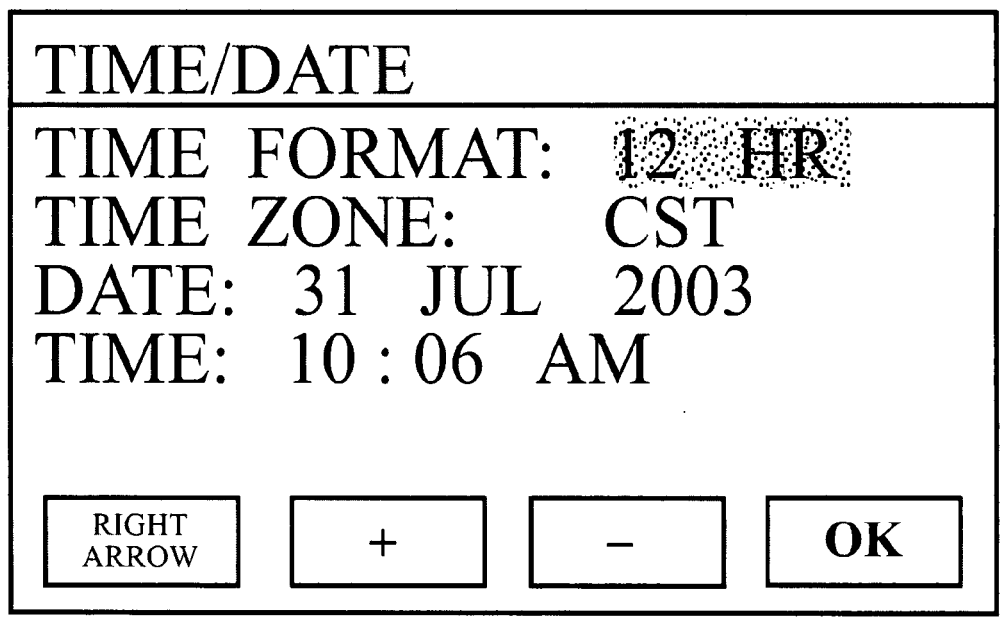
FIG. 5 is a Set Time/Date screen.

To set the time and date, the patient moves the highlight to "time/date" and presses the Select key. The Set Time/Date screen is displayed as shown in FIG. 5. The patient presses the Right Arrow key to move the highlight through the modifiable fields. When the patient presses the + key and − key, the currently highlighted field will change values accordingly.

The patient chooses between a 12 hour or 24 hour format, selects the correct time zone, and sets the date and time for the real time clock chip that is part of microcontroller 68. Once the real time clock is set, the patient presses the Ok key to update the time settings and return to the System screen. Base station 22 may also be programmed to retrieve the time and date from server 34 once it is plugged into network 30.

Figure 6:
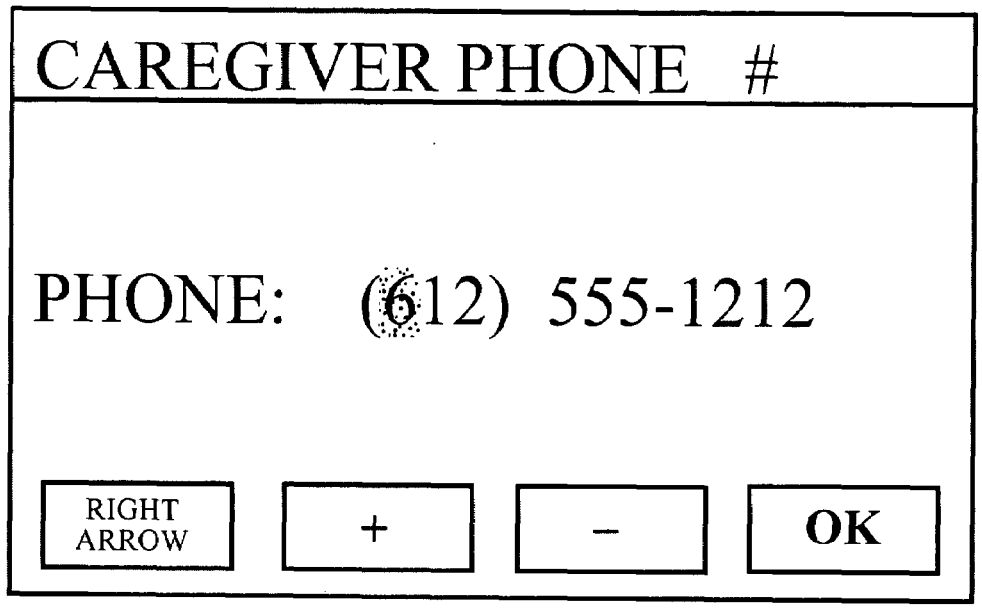
FIG. 6 is a Set Care giver Phone # screen.

Next, from the System screen, the patient selects "care giver phone #," and the Set Care giver Phone # screen is displayed, as shown in FIG. 6. The Set Care giver Phone # screen displays the telephone number of the primary care giver in case they need to be contacted. When initially entered, the first character of the area code is highlighted. The patient presses the + key and − key to change the value of the highlighted character. The Right Arrow key moves the highlight to the next character. When finished, the patient presses the Ok key to update the care giver telephone number and return to the System screen.

The patient must then provide information regarding the Internet service provider (ISP) by selecting "ISP information." Once selected, the Set ISP Information screen is displayed as shown in FIG. 7. The patient must set the telephone number, login, and password for the ISP that transfers the data to the server application.

When initially entered, the first character of the area code is highlighted. The + key and − key change the value of the currently highlighted field accordingly. The Right Arrow key moves the highlight to the next modifiable field. The patient presses the Ok key to update the ISP information and return to the System screen.

Figure 8:
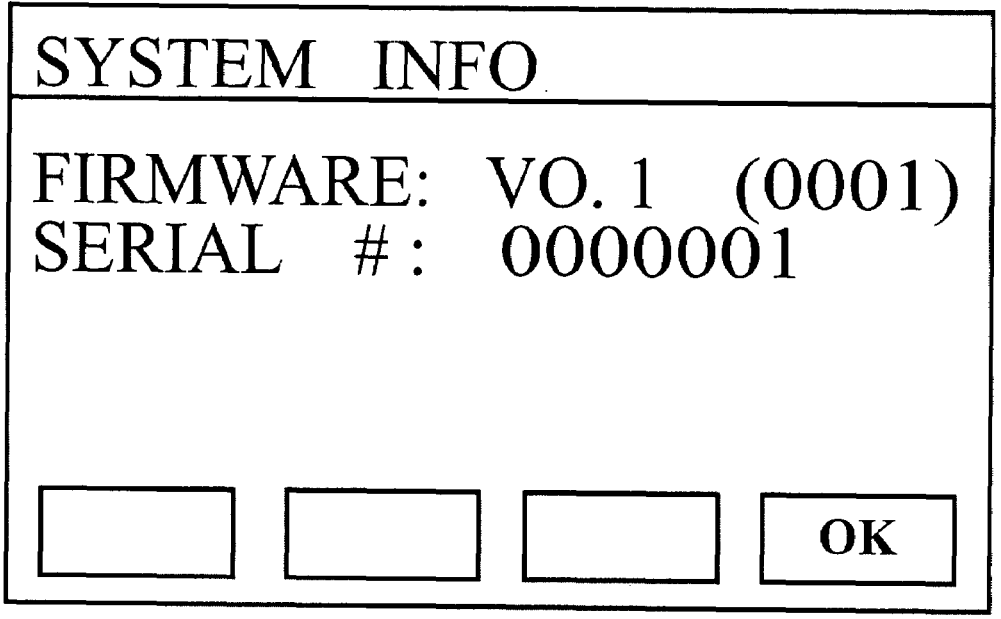
FIG. 8 is a System Info screen.

The patient may also view "system information" for base station 22 by selecting it on the System screen. When selected, the System Information screen is displayed as shown in FIG. 8. The System Information screen displays the firmware version, build number, and serial number of base station 22. The patient presses the Ok key to return to the System screen. Base station 22 is ready once the updates are set.

Figure 9:
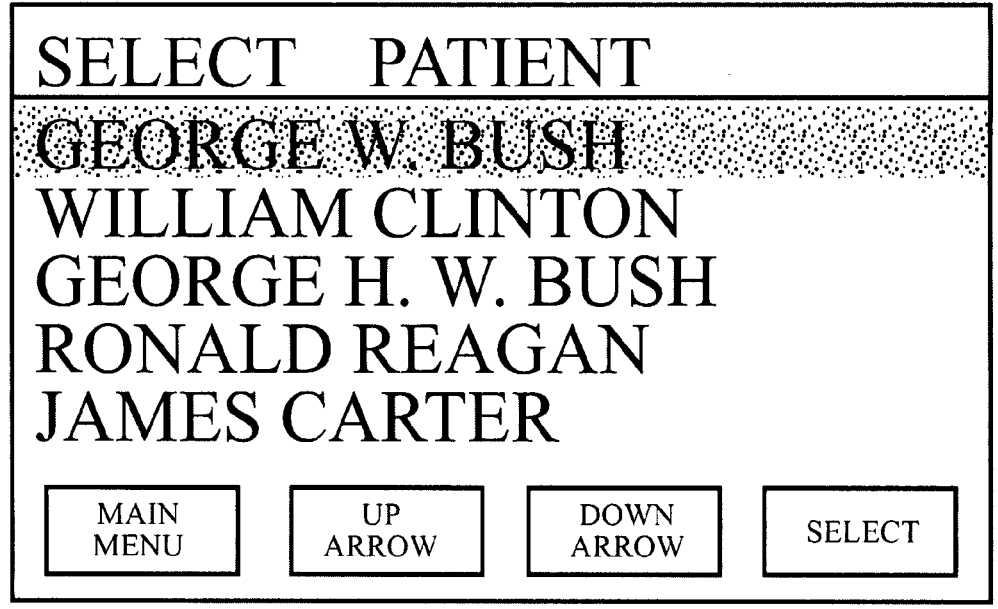
FIG. 9 is a Select Patient screen.

The medication-taking and compliance data are viewable on base station 22. When the Select Patient key is pressed on the Main Menu screen the Select Patient screen is displayed as shown in FIG. 9. System 10 can be used for a plurality of patients each taking a plurality of medications. When initially entered the first patient in the list is highlighted, and the patient presses the Up Arrow key and the Down Arrow key to move the highlight up and down the list, respectively. When the patient presses the Select key, the Patient Medication screen is displayed for the currently highlighted patient. The Main Menu key is pressed to return to the Main Menu screen.

Figure 10:
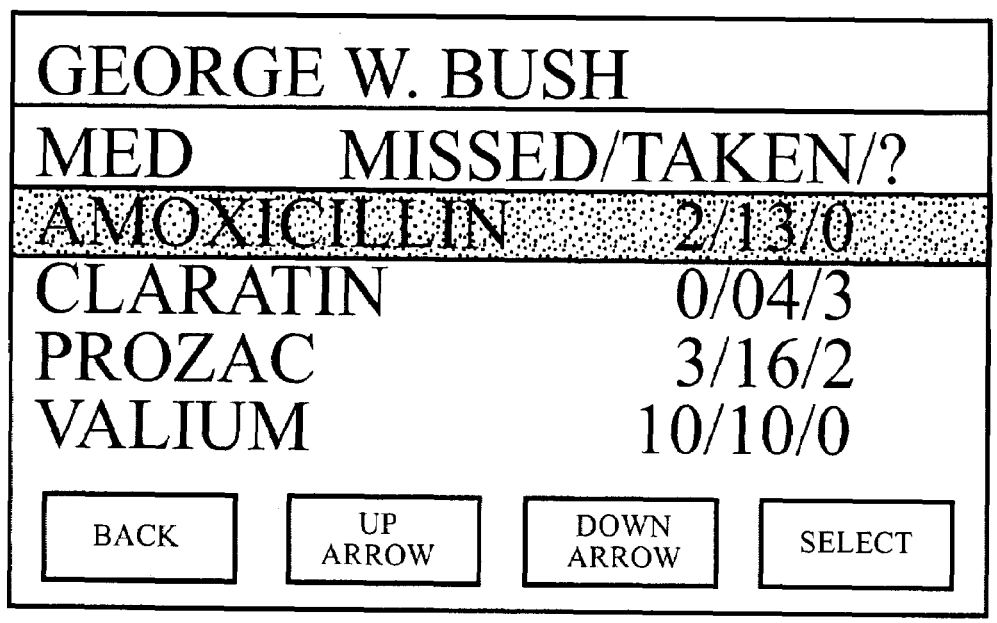
FIG. 10 is a Patient Medication screen.

The Patient Medication screen is shown in FIG. 10. The Patient Medication screen lists all the medications that the selected patient is taking. It also includes compliance data for each medication. The first medication in the list is initially highlighted, and the patient presses the Up Arrow key and Down Arrow key to move the highlight. When the patient presses the Select key, the Medication History screen is displayed for the selected medication. Pressing the Back key returns to the Select Patient screen.

FIG. 11 shows the Medication History screen, which lists all the dosages that have been taken and missed (compliance data). The first dose information is highlighted when the Medication History screen is initially entered, and the patient can press the Up Arrow and Down Arrow keys to move the highlight. When the Details key is pressed, the Medication Detail screen is displayed. The Back key displays the Patient Medication screen.

Figure 12:
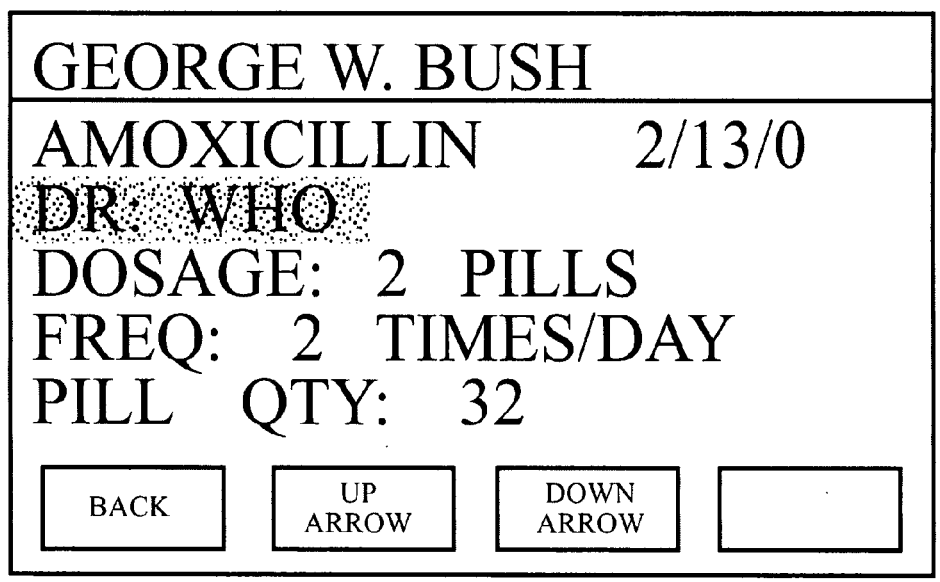
FIG. 12 is a Medication Detail screen.

The Medication Detail screen is shown in FIG. 12. The Medication Detail screen lists all the medication-taking data and a summary of the compliance data. The Up Arrow and Down Arrow keys move the highlight up and down the list. The Back key displays the Medication History screen. With this and all the screens described for base station 22, five minutes of inactivity results in the Main Menu screen being displayed.

Base station 22 is connected to network 30 by either modem 28a or interface 28b, and base station 22 may be equipped with either or both. The physician can subsequently retrieve the compliance data whenever it is convenient to do so without having to wait for data from the patient or having to travel to the patient. Proprietary software allows the physician, care giver, etc., to view the information sent by base station 22. The software is designed with the ability to generate custom reporting. In addition, the compliance data generated by the present invention is much more reliable than the patient's memory or relying on the patient to note compliance.

Figure 13:
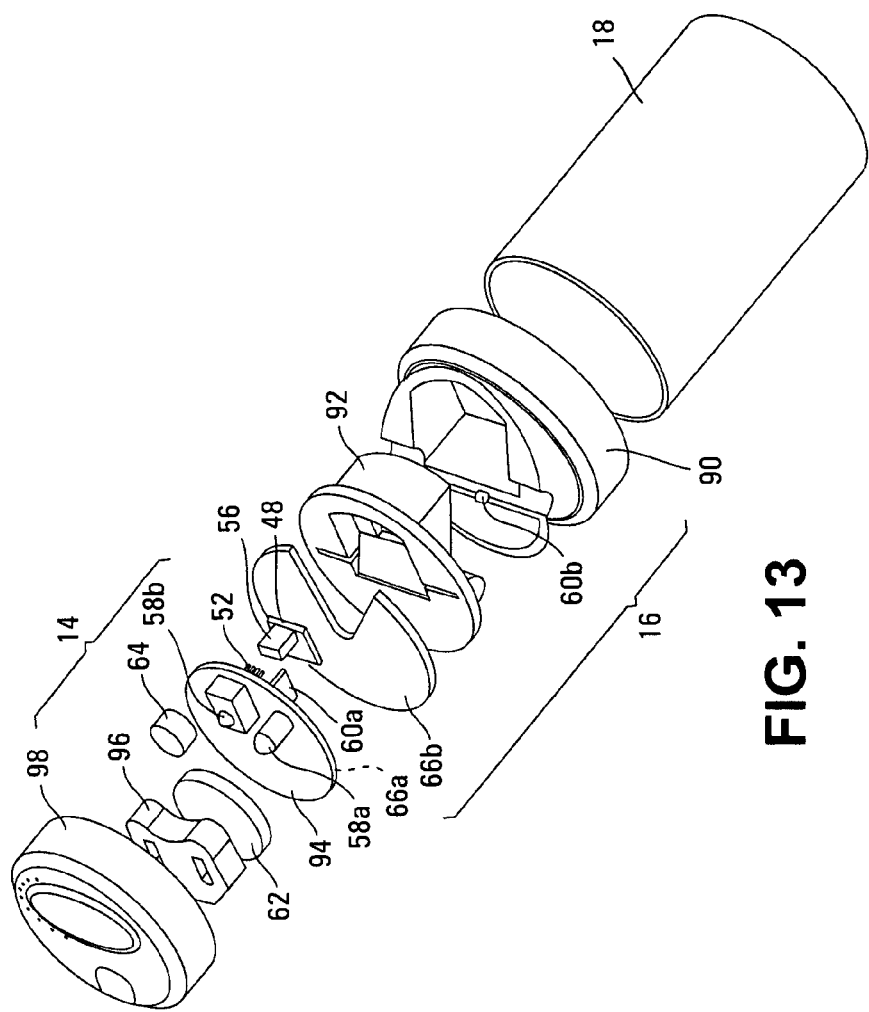
FIG. 13 is an exploded view of the portable medication dispenser.

FIG. 13 shows dispenser 12 in more detail. Dispenser 12 includes container 18, collar 16, and cap 14. Collar 16 further includes memory 48, connector 56, magnet 60b, stationary base 90, and pivoting base 92. Cap 14 further includes connector 52, IR transmitter 58a, IR receiver 58b, switch 60a, battery 62, audio indicator 64, LED lamp 66a, illuminated disc 66b, board 94, battery clip 96, and top 98.

Collar 16 attaches to container 18. Memory 48 and connector 56 are mounted on pivoting base 92.

Cap 14 attaches to collar 16. Connector 52, switch 60a, LED lamp 66a, and illuminated disc 66b are mounted on the underside of board 94. IR transmitter 58a and IR receiver 58b are mounted on the topside of board 94 near battery 62 and audio indicator 64. Microcontroller 44 (not shown) is also mounted on board 94. Battery clip 96 holds battery 62, or battery 62 may be mounted to board 94. Top 98 covers the internal components of cap 14.

Figure 14:
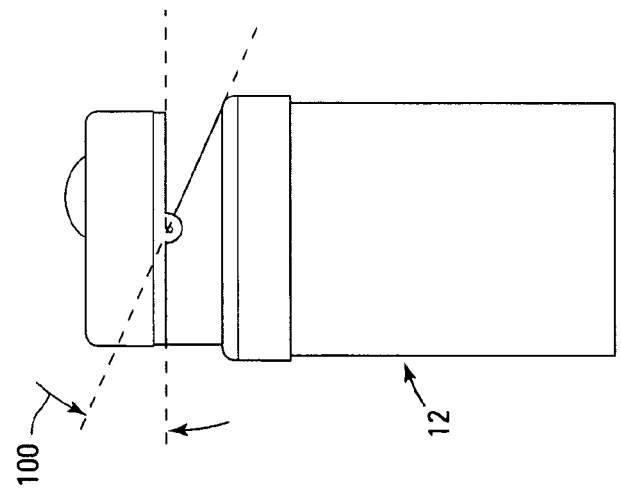
FIG. 14 is a side view of the portable medication dispenser.

In operation, container 18 is filled with medication, and collar 16 with cap 14 is attached adjacent the opening of container 18. When it is time for the patient to take a dose of medication, LED lamp 66a is activated to illuminate illuminated disc 66b, and/or audio indicator 64 is activated to notify the patient. The patient simply presses down on cap 14 such that pivoting base 92 pivots relative to stationary base 90 of collar 16 as shown in FIG. 14. FIG. 14 shows shaded region 100, which is the pivot range for opening dispenser 12. Preferably, the pivot range is about 0.4 in. The patient dispenses a dose of medication and closes the portable cap assembly.

Switch 60a and magnet 60b form sensor 60 for sensing the opening/closing of dispenser 12. Switch 60a is a dry reed switch. As pivoting base 92 pivots open, switch 60a changes state to generate an electrical signal by contacting magnet 60b. When pivoting base 92 returns to its original position, switch 60a is no longer in contact with magnet 60b, and the signal stops. Thus, microcontroller 54 automatically knows that the patient complied with the medication regimen without the patient having to remember to indicate that a dose was taken.

Top 98, in the present embodiment, is transparent to allow for passage of IR signals. If another means of wireless communication is utilized, top 98 does not need to be transparent. Top 98 may also be equipped with a child proof lock mechanism.

The present invention is a device and system that reminds patients to comply with a medication-taking regimen. This is particularly helpful when many medications are being taken and/or when a patient tends to be forgetful. The present invention also allows the physician to track the patient's compliance without having to rely on the patient to do so, and the physician can obtain the compliance data from a remote location.

Although the present invention has been described with reference to preferred embodiments, workers skilled in the art will recognize that changes may be made in form and detail without departing from the spirit and scope of the invention.

The invention claimed is:

1. A medication compliance device comprising:
a base station having a local wireless communication link, user interface and a memory;
a portable cap assembly for association with a container of medication, the portable cap assembly comprising:
a local wireless communication link;
a memory;
an indicator;
a sensor;
a cap;
a collar between the can and an opening of the container for attaching the cap to the container, the collar including the memory of the cap assembly and a movable base movable relative to the container while the collar is attached to the container from a first position in which the opening is substantially covered to a second position in which the opening is exposed for dispensing medication from the container; and
a controller for directing the communication link to receive and transmit medication-taking data for directing the memory to store the medication-taking data, for directing the indicator to activate according to the medication-taking data, for directing the sensor to gather and the memory to store compliance data that indicates whether the sensor sensed that a user has taken a plurality of doses of the medication in compliance with the medication-taking data, and for directing the local wireless communication link to transmit the compliance data to the base station,
wherein the base station receives the compliance data from the cap assembly via the local wireless communication link, stores the compliance data in the memory of the base station, and presents the compliance data via the user interface.

2. The device of claim 1 wherein the medication-taking data further comprises a medication-taking regimen.

3. The device of claim 1 wherein the portable cap assembly further comprises:
a transparent top with a child-proof lock mechanism.

4. The device of claim 1 wherein the communication link comprises infrared light emitting diode.

5. The device of claim 1 wherein the base station transmits the compliance data to a remote location through a data network.

6. The device of claim 1 wherein the indicator comprises at least one of a visual indicator, an audible indicator, or a tactile indicator.

7. The device of claim 5, wherein the data network is coupled to a data server for storing data far the device.

8. The device of claim 1, wherein the base station receives compliance data for a plurality of users.

9. The device of claim 1, wherein the base stations receives compliance data for a plurality of medications.

10. A medication compliance system comprising:
a portable cap assembly for attaching to a container, the cap assembly having
memory for storing medication-taking data and compliance data,
local wireless communication for transmitting the medication-taking data and compliance data, a first indicator for indicating when a user should take a dose of medication stored in the container based on the medication-taking data,
a sensor for sensing that the user has taken the dose of medication,
a collar connected adjacent an opening of the container and including the memory of the portable cap assembly, wherein the collar is positioned between the cars and the opening,
a cap removably attached to the collar, and
a movable base that moves relative to a stationary base of the collar from a first position in which the opening is substantially covered to a second position in which the opening is exposed for dispensing the medication from the container,
wherein the sensor senses cap movement due to movement of the movable base, which is stored as compliance data, and
wherein the compliance data stored in the memory indicates whether the sensor sensed that the user has taken a plurality of doses of medication in compliance with the medication-taking data; and
a base station that supports local wireless communication for receiving the medication-taking data and the compliance data from the portable cap assembly, base station memory for storing the medication-taking data and the compliance data, a user-interface for presenting the compliance data, and wired communication for transmitting the compliance data to a remote location.

11. The system of claim 10 wherein the base station is programmed with medication-taking data from a remote location.

12. The system of claim 10 and further comprising:
a computer terminal electrically coupled to the programming station for programming the portable cap assembly with the medication-taking data.

13. The system of claim 10 wherein the base station further comprises:
a second indicator for Indicating when the user should take the dose of medication based on the medication-taking data received from the cap; and
wherein the second indicator is activated when the cap is within a range for local wireless communication with the base station.

14. A medication compliance device comprising:
a collar for attaching adjacent an opening of a medication container, the collar having a first communication link, a memory for storing medication-taking data and compliance data, a stationary base adjacent the opening of the container, and a movable base coupled to the stationary base, wherein the movable base moves relative to the stationary base while attached to the stationary base from a first position in which the opening is substantially covered to a second position in which the opening is exposed to dispense medication from the container; and
a cap attached to the collar such that the collar is between the cap and the opening, the cap further comprising:
a first communication link;
an indicator for inducing compliance with the medication-taking data;
a sensor for sensing compliance with the medication-taking data;
a microcontroller for engaging communication with the collar through the communication link, activating the indicator according to the medication-taking data, gathering the compliance data regarding a plurality of sensed compliance events from the sensor, and storing the compliance data in the memory of the collar via the first communication link,
wherein the movable base is coupled to the stationary base between the opening and the cap, and the sensor senses movement of the movable base.

15. The device of claim 14 wherein the cap further comprises:
a second communication link for transmitting the medication-taking data and compliance data such that the data is accessible through a data network.

16. The device of claim 14 wherein the collar further comprises:
a second communication link for receiving the medication-taking data.

17. The device of claim 14 wherein the indicator is a visual indicator.

18. The device of claim 14 wherein the indicator is an audio indicator.

19. The device of claim 14, wherein the movable base comprises a pivoting base that pivots relative to the stationary base.

20. The device of claim 15, wherein the data is accessible through the data network through use of proprietary software for programming a remote terminal, tracking the medication-taking data and compliance data, displaying the medication-taking data and compliance data, and generating custom reports.

* * * * *

UNITED STATES PATENT AND TRADEMARK OFFICE
CERTIFICATE OF CORRECTION

PATENT NO. : 7,295,890 B2 Page 1 of 1
APPLICATION NO. : 10/670595
DATED : November 13, 2007
INVENTOR(S) : Jean-Pierre It is certified that error appears in the above-identified patent and that said Letters Patent is hereby corrected as shown below:

On Column 11, line 3, (Claim 13), "Indicating" should read --indicating--.0

Signed and Sealed this

Third Day of June, 2008

JON W. DUDAS
*Director of the United States Patent and Trademark Office*